United States Patent [19]

Frech et al.

[11] 4,435,371

[45] Mar. 6, 1984

[54] SULFUR REMOVAL FROM A GAS STREAM

[75] Inventors: Kenneth J. Frech, Tallmadge; James J. Tazuma, Stow, both of Ohio

[73] Assignee: The Goodyear Tire & Rubber Company, Akron, Ohio

[21] Appl. No.: 352,812

[22] Filed: Feb. 26, 1982

[51] Int. Cl.³ .............................................. B01D 53/34
[52] U.S. Cl. ..................................... 423/228; 423/229; 423/230; 423/231; 423/234; 423/244; 423/573 R
[58] Field of Search ............... 423/230, 231, 224, 234, 423/244, 573, 571, 228, 229

[56] References Cited

U.S. PATENT DOCUMENTS

| 4,238,463 | 12/1980 | Nicksic | 423/231 |
| 4,278,646 | 7/1981 | Lynn et al. | 423/226 |
| 4,283,373 | 8/1981 | Frech et al. | 423/230 |
| 4,311,680 | 1/1982 | Frech et al. | 423/230 |

FOREIGN PATENT DOCUMENTS

| 233011 | 5/1925 | United Kingdom | 423/231 |

*Primary Examiner*—Earl C. Thomas
*Attorney, Agent, or Firm*—D. O. Nickey

[57] ABSTRACT

There is disclosed a process for removing sulfur compounds from a gas stream. The process involves passing the gas stream containing the sulfur compounds through a mass of porous material that has deposited upon it a metal oxide, the improvement comprises the continuous or intermittent addition of an oxidizing agent and an amine.

11 Claims, No Drawings

SULFUR REMOVAL FROM A GAS STREAM

CROSS-REFERENCE TO RELATED APPLICATION

This invention is related to our patent application Ser. No. 208,613 for a Method For Removal Of Sulfur Compounds From A Gas Stream. More specifically, this invention describes an improved method for the sweetening of the sour natural gas stream.

TECHNICAL FIELD

This invention relates to a process for the removal of sulfur compounds such as $H_2S$ mercaptans, sulfides and disulfides from a gas stream. More specifically, this invention describes an improved method for the sweetening of a sour natural gas stream.

BACKGROUND ART

Removal of sulfur compounds from gas streams has been of considerable importance in the past and is even more so today due to environmental considerations. Gas effluent from the combustion of organic materials, such as coal, almost always contain sulfur compounds and sulfur removal processes have concentrated on removing hydrogen sulfide since it has been considered a significant health hazard and because it is corrosive, particularly when water is present. With increasing emphasis on eliminating or minimizing sulfur discharge to the atmosphere, attention is turning to removal of other sulfur compounds from gas streams.

Sulfur contaminants in natural gas streams include hydrogen sulfide, mercaptans, sulfides, and disulfides which due to their odorous nature can be detected at parts per million (ppm) concentration levels. Thus, it is desirable for residential and commercial users of natural gas to have concentrations of mercaptans lowered to 1 ppm and total concentrations of sulfur compounds to 20 ppm or less.

Numerous natural gas wells produce what is called in the industry as "sour gas." "Sour gas" is natural gas that contains hydrogen sulfide, mercaptans, sulfides and disufides in concentrations that make its use unacceptable. Considerable effort has been expended to find an effective and cost efficient means to remove these objectionable sulfur compounds from natural gas.

Transmission companies that purchase natural gas from well owners and then distribute to consumers are very critical of sulfur content and require total sulfur content to be less than 30 ppm. Thus, owners of sour gas wells that exceed the 30 ppm limit are constantly searching for new and more efficient means to make their gas salable.

A number of processes are known for the removal of $H_2S$ from natural gas streams. Processes presently available can be categorized as those based on physical absorption, solid absorption or chemical reaction. Physical absorption processes suffer from the fact that they frequently encounter difficulty in reaching the low concentration of hydrogen sulfide required in the sweetened gas stream. Solid bed absorption processes suffer from the fact that they are generally restricted to low concentrations of $H_2S$ in the entering gas stream. Chemically reacting processes in general are able to meet sweet gas specifications (primarily $H_2S$ concentrations) with little difficulty; however, they suffer from the fact that a material that will react satisfactorily with $H_2S$ will also react with $CO_2$. Above all, the processes presently available do not effectively provide for the removal of mercaptans, sulfides and disulfides.

An example of a chemically reactive process is the ferric oxide fixed bed process, wherein the reactive entity is ferric oxide ($Fe_2O_3$) impregnated on an inert carrier. This process is good for the removal of $H_2S$ but does not appreciably remove mercaptans or other sulfur compounds. The bed can be regenerated; however, the number of regenerations is limited by the buildup of elemental sulfur upon the bed.

The iron oxide or "dry box" process was one of the first developed for removing $H_2S$ from gas streams. It was introduced in England about the middle of the 19th century and is still widely used in many areas in special applications. See U.S. Pat. Nos. 632,400 and 1,934,242.

The iron sponge method of sulfur removal from natural gas has been widely used during the past quarter century and has been reported in detail in the literature. See, for example, Taylor, D. K., "High Pressure Dry Box Purification;" Proceedings Gas Conditioning Conference, University of Oklahoma, 1956, page 57; and The Oil and Gas Journal, November and December 1956, a series of 4 articles; and Zapffe, F., "Practical Design Consideration For Gas Purification Processes," The Oil and Gas Journal, Sept. 8, 1958, page 100; and Sept. 10, 1962, page 135.

Typically, the iron oxide process apparatus is two towers filled with an inert carrier that is impregnated with iron oxide. Each tower has a means for the injection of water and air so as to allow for regeneration. Ordinarily at least two iron oxide beds will be used in order to provide for continuous operation. "Sour gas" enters the top of the bed and flows downward contacting the iron oxide. Sweetened gas is removed from the bottom of the vessel. The vessel not in operation would normally be shut down for removal or regeneration of the exhausted iron oxide. In the piping and operation of the process, provisions must be made for the introduction of water and maintenance of a slightly basic pH. Water must be added to this process or the gas will gradually dehydrate the ferric oxide, thus causing it to lose its activity.

There are several known forms of ferric oxide. The ferric oxide is dispersed on materials of large surface and light weight. The most frequently used material is wood shavings or chips. Dispersing the iron oxide in this way provides a relatively large suface area to weight ratio and maximizes contact between the gas stream and the iron oxide.

The iron oxide process can be operated on a batch basis or continuously, the difference depending upon the technique used for regeneration. When a batch process is used the tower is operated until the bed becomes saturated with sulfur and $H_2S$ begins to appear in the sweetened gas stream. At this point the tower is removed from sweetening service and regenerated by circulating gas containing a small amount of air through the bed. Oxygen concentration of the regeneration stream is normally held below 3 percent because of the highly exothermic nature of the regeneration reaction. In continuous service a small concentration of oxygen may be added to the "sour gas" before entry to the bed. The oxygen in the air reacts with iron sulfide previously formed to regenerate it at the same time ferric oxide is reacting with $H_2S$ in the gas. Each system has advantages and disadvantages and the choice between batch regeneration and continuous regeneration is based on economic factors which differ from installation to installation.

Theoretically, one pound of ferric oxide will react with 0.65 lbs. of hydrogen sulfide, In field operation this level is never reached. Generally, at 80–85% of theory, $H_2S$ will begin to break through and show up in the gas stream. At this point the bed is shut down and regenerated. For continuous regeneration, D. K. Taylor, *The Oil and Gas Journal*, 54, 125 (Nov. 5, 1956); 54, 260 (Nov. 19, 1956); 54, 139 (Dec. 3, 1956); 54, 147 (Dec 10, 1956); reports that about 2.5 lbs of sulfur may be removed per pound of iron oxide before the oxide must be replaced.

In natural gas service, pressures are normally high and pressure drop through the bed is not a serious factor.

It has been reported that cycle time of an iron sponge unit in the field is usually 30 days. A long cycle time is desired to minimize bed replacement costs. Regardless of the regeneration methods that are employed today, the bed will eventually plug with sulfur and have to be replaced. This required manual labor which is expensive. Taylor, in the reference above, gives an excellent summary of points to consider in the design of towers for an iron oxide process for ease of bed replacement and operation.

Primarily, the iron sponge process has been applied to the removal of hydrogen sulfide. The iron sponge will also remove minute amounts of mercaptans from a natural gas stream but this process is not well characterized nor is it efficient.

The affinity of iron oxide for hydrogen sulfide and mercaptans is quite different. While the iron oxide has a strong persistent affinity for hydrogen sulfide, its capacity for removal of mercaptans in the presence of hydrogen sulfide is much lower. This results in "break out" of mercaptans in the early stages of metal oxide bed life. Thus, in order to maintain the desired level of sulfur compounds in the treated stream it is necessary to periodically regenerate the oxide. The data obtained utilizing the process of the present invention indicates that this is very efficiently carried out by periodic or continuous treatment of the oxide bed with an oxidizing agent and an amine, which also provides an unexpected improvement in the oxide's ability to remove mercaptans.

U.S. Pat. No. 4,278,646 discloses a method wherein hydrogen sulfide is removed from a gas stream by contacting the stream with an aqueous solution of ferric ion chelated with an aminopolycarboxylic acid at a pH of 3.5 to 5. This patent discloses a method wherein an aqueous solution of iron chelated with an aminopolycarboxylic acid is used to remove $H_2S$ from a gas stream. The solution also contains ammonia or an aliphatic, alicyclic or heterocyclic primary or secondary amine in a proportion sufficient to prevent precipitation of iron from the solution.

U.S. Pat. No. 4,238,463 discloses a method for the removal of hydrogen sulfide from gases using iron oxide, wherein a liquid containing a primary or secondary amine is introduced onto the iron oxide-containing solids. This patent utilizes an amine to prevent the treatment beds from hardening into a cohesive mass which is resistant to conventional removal means. Specifically, U.S. Pat. No. 4,238,463 disclosed the addition of a primary, or preferably a secondary amine, to a bed of iron sponge. In addition, U.S. Pat. No. 4,238,463 uses the amine as a solution or suspension of an amine, such as a water solution, but it is preferably a nonaqueous liquid having the amine in solution. A preferred nonaqueous solvent is dimethylsulfoxide. Further, the aqueous solution of the amine was added to the soda ash liquid normally used to maintain an alkaline condition in the bed. The amine solution was then added to the iron sponge every seven days. This patent does not suggest or disclose the beneficial effects of concurrently or intermittently adding an amine, such as ammonia hydroxide, and an oxidant to the iron sponge bed, to accomplish economical and effective removal of sulfur compounds from a gas stream.

A process which improves the ability of an iron sponge to remove sulfur compounds from a gas stream is in demand. The process of the present invention accomplishes effective and economical removal of sulfur compounds from a gas stream through the use of an oxidizing agent and an amine in combination with a metal oxide treatment bed. The reaction of ferric oxide with hydrogen sulfide has been well documented, however, the literature and publications do not disclose or suggest a method in which an oxidizing agent and an amine are added to a metal oxide bed so as to enhance the ability of the oxide bed in the removal of $H_2S$ and mercaptans from a gas stream. Further, the literature and the referred to patents do not suggest or disclose the fact that the use of an amine and an oxidant exhibit a synergistic effect.

It is the novel and unobvious use of an oxidizing agent and an amine in a process to remove sulfur compounds from a gas stream that comprises at least a portion of the present invention.

DISCLOSURE OF THE INVENTION

There is disclosed a process for removing hydrogen sulfide, sulfides and mercaptans from gas streams which comprises the steps in combination of:
(a) contacting the gas stream with an oxide of a metal selected from the group comprising iron, chromium, cobalt, lead, manganese, molybdenum, nickel, copper, vanadium, zinc, tungsten and antimony;
(b) introducing an amine, continuously or intermittently, of the structural formula:

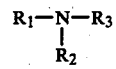

wherein $R_1$, $R_2$ and $R_3$ are selected from the group comprising hydrogen, alkyls of 1 to 8 carbon atoms and alkanols of 1 to 8 carbon atoms with the proviso that $R_1$, $R_2$ and $R_3$ cannot all be hydrogen; in anhydrous form, aqueous solutions or water/alcohol solutions thereof, onto the metal oxide; and
(c) subsequently or concurrently introducing an oxidizing agent, continuously or intermittently, selected from the group comprising oxygen, hydrogen peroxide, air, tertiary dibutyl peroxide, t-butyl hydroperoxide, cumene hydroperoxide and dicumyl peroxide, on the metal oxide while continuing to contact the gas stream with said metal oxide.

There is also disclosed a process for removing hydrogen sulfide, sulfides and mercaptans from a gas stream which comprises the steps in combination of:
(a) contacting the gas stream with an oxide of a metal selected from the group comprising iron, chromium, cobalt, lead, manganese, molybdenum, nickel, copper, vanadium, zinc, tungsten, and antimony;

(b) introducing ammonia onto the metal oxide; and (c) subsequently or concurrently introducing hydrogen peroxide onto the metal oxide while continuing to contact the gas stream with the metal oxide. Of the metal oxides that are more useful in the process of the present invention are oxides of iron, cobalt and copper. Expecially preferred and useful in the process of the present invention is iron oxide ($Fe_2O_3$).

The applicants have found that ferric oxide deposited upon an inert material such as activated carbon, vermiculite and wood chips is presently the most economical and commercially available means of utilizing the metal oxides in the process of the present invention. In addition, it has been found necessary that the ferric oxide have and maintain either the alpha or gamma forms.

Representative of the oxidizing agents that are useful in the process of the present invention are oxygen, hydrogen peroxide, air, tert-dibutyl peroxide, t-butyl hydroperoxide, cumene hydroperoxide, dicumyl peroxide and other commercially available organic peroxides and hydroperoxides. The most preferred oxidizing agent is hydrogen peroxide.

Representative of the amines that are useful in the process of the present invention are methyl amine, dimethyl amine, ethyl amine, diethyl amine, ethanol amine, diethanol amine, propanol amine and dipropanol amine. Preferred amines are methyl amine, dimethyl amine, trimethyl amine and diethanol amine. The most preferred nitrogen containing compound is ammonia.

The amine which is added to the oxide bed in the process of the present invention may be anhydrous, aqueous solutions of the amine or water/alcohol solutions of the amine. Alcohols of one to four carbon atoms are useful in preparing the water/alcohol amine solutions. Such alcohols include methanol, ethanol, propanol, isopropanol, butanol and isobutanol.

The concentration of an amine solution being pumped onto the oxide bed is preferably saturated or highly concentrated solutions thereof. It has been found that concentrations of 0.1 Normal to saturated solutions are appropriate; however, the more concentrated solutions are preferred. In fact, the addition of anhydrous ammonia or other anhydrous amines is advantageous since lower concentrations only result in the unnecessary addition of liquid material to the treatment bed which eventually has to be removed.

It has been found that the process of the present invention also prevents the oxide bed from hardening into a cohesive mass which is resistant to conventional removal means.

The use of the alcohol cosolvent in the preparation of the water/alcohol amine solution is only required when the amines have limited water solubility. Only when the amine has limited water solubility should the alcohol cosolvent be used.

To one skilled in chemistry it is readily apparent that anhydrous amines, or anhydrous ammonia, will, when placed in an aqueous media, form the hydrates thereof, i.e., aqueous ammonia as well as ammonia hydroxide. The process of the present invention contemplates these hydrates and has found the use of ammonia dissolved in water to be especially useful.

The applicants have found that the use of a caustic solution in the process of the present invention is not necessary, but useful in solubilizing the reaction products from the reoxidation of the treatment bed. Aqueous solutions of NaOH, KOH and $Na_2CO_3$ have been found to be appropriate.

There is also disclosed a process for removing $H_2S$, mercaptans, sulfides and disulfides from a gas stream wherein said gas stream is contacted with at least one metal oxide deposited upon an inert carrier, the improvement comprising continuously or periodically introducing an oxidizing agent and amine on the metal oxide while continuing to contact the gas stream with said metal oxide.

Further, the process of the present invention provides a means to extend the useful life of a metal oxide bed in the removal of sulfur compounds from a gas stream which comprises the addition of an oxidizing agent and an amine to the oxide bed.

Use of the ferric oxide system as taught in the literature is dependent on hydrate formation for maximum activity and is susceptible to difficulties in regeneration. Presently, commercial "state of the art" methods exist whereby iron sponge bed can be regenerated. This is accomplished in two ways: (1) constant onstream regeneration by introduction of air (oxygen) through a compressor blower to obtain an oxygen level based on the gas flow of up to 2 percent; and (2) offstream regeneration of the bed by introduction of air by compressor blower over a period of 8 hours or until virtually all the iron sulfides have been converted to oxides. Both methods are costly as they require high power consumption and have high capital requirements. In addition, both methods do not provide water to maintain the optimum state of hydration and the offstream addition of regeneration air interrupts production.

The present invention (1) allows the iron oxide to maintain a high state of reactivity in an onstream manner; (2) increased bed life; (3) reduces the chemical requirements in a secondary treater, if used; (4) accomplishes sulfur removal from the gas stream without resorting to costly compressor blower systems which require high power/labor requirements; and (5) provides a means of maintaining the metal oxide bed at an optimum level of hydration.

The process of the present invention can be employed with or without the use of a secondary treater. By secondary treater is meant a treatment process which further eliminates or reduces the amount of sulfides and disulfides in the gas stream, subsequent to treatment by the process of this invention. Examples of said secondary treatments can be found in applicants' U.S. Pat. No. 4,283,373, entitled "Method for Removal of Sulfur Compounds From A Gas." Said U.S. Pat. No. 4,283,373 is herein incorporated by reference to this present application.

The temperature of the treatment system is maintained at a temperature of at least 0° C., to prevent water vapor from freezing; however, a more preferred temperature range is from 5° to 80° C., with the most preferred range being from 5° to 35° C.

The gas flow rate and the volume of the treater is such that the retention time in the treater is sufficient to remove a major portion of the $H_2S$, mercaptans, sulfides and disulfides from the gas stream.

Those skilled in the art will readily be able to determine the values of the variables in the treatment so as to substantially reduce sulfur content in the gas stream.

A basic solution such as aqueous NaOH or soda ash can be employed in the treatment vessel. Alkalinity is preferred so as to assist the regeneration of the ferric oxide bed.

The use of a secondary treater in the process of this invention is not essential; however, such use may be needed if the sulfur load or composition of the gas stream (sulfur compounds) is such that the primary treater or process of the present invention is unable to remove the necessary amount of sulfur compounds from the gas stream to meet the desired specification.

The process of this invention was tested on a high pressure natural gas stream. There would be minor modifications in the process flow for use of a low pressure gas such as coke oven gas or boiler gas. However the basic principles of operation would remain the same.

The process of the present invention overcomes the limiting capacity of metal oxides (especially iron oxide) treatment for a variety of sulfur compounds. The process of this invention enhances this capacity by the use of an oxidant such as hydrogen peroxide and an amine, such as ammonia.

To one skilled in the art, the amount and concentration of the oxidant sprayed onto the treatment bed can be easily determined. Specifically, enough aqueous oxidant should be used so as to lower the sulfur content of the gas stream to a predetermined level. Excess usage of oxidant (i.e., $H_2O_2$) can be prevented by use of stoichiometric calculations based on input gas analysis.

Low concentrations of $H_2O_2$ (i.e., less than 25%) can be used in the process of this invention; however, several problems can be encountered:
(1) excessive water flow through the bed will cause the $Fe_2O_3$ coating on the bed to be washed off causing pipe plugging problems;
(2) where sub 0° C. temperatures are encountered, low concentrations of $H_2O_2$ freeze (i.e., 20 percent freezes at $-7°$ C.);
(3) increased cost of transporting $H_2O_2$ to the treatment site.

High concentrations of aqueous $H_2O_2$ (i.e., greater than 90%) are suitable for use in the process of this invention; however, extreme caution must be exercised in the field when such high concentrations of $H_2O_2$ are used. In addition, the freezing point of 90% aqueous $H_2O_2$ is only $-12°$ C. and will therefore limit the application.

The applicants have discovered that pumping amounts of at least 25% $H_2O_2$ and concentrated ammonium hydroxide on the iron sponge treatment bed will not only provide for the reactivation of the iron sponge but also assist in the removal of sulfur compounds such as mercaptans, sulfides and disulfides. Additionally, use of $H_2O_2$ and an amine unexpectedly provides residual capability for removing sulfur compounds long after $H_2O_2$ addition has ceased.

As discussed earlier, the reaction of hydrogen sulfide with ferric oxide is well-known; however, all the references and other literature would lead one skilled in the art to believe that use of an oxidant such as $H_2O_2$ would not be possible due to the thermodynamic and kinetic limitations of the reaction of $H_2O_2$ with ferric sulfide and directly with $H_2S$ and/or mercaptans. The literature discloses air oxidation of the ferrous sulfide back to ferrous oxide with long reaction times and equilibria for short of complete rejuvenation.

One may make the argument that use of $H_2O_2$ in place of oxygen or air for the rejuvenation of the ferric oxide bed would be obvious, since two molecules of $H_2O_2$ degrade to 2 molecules of $H_2O$ and one of $O_2$. Thus, one skilled in the art would expect $H_2O_2$ to provide the same results that air or $O_2$ injection would provide. The applicants have discovered, however, that use of $H_2O_2$ to regenerate the ferric oxide bed in combination with an amine provides an unexpected suynertistic effect in that removal of $H_2S$ and mercaptans, by the iron sponge bed is enhanced and prolonged.

The use of $H_2O_2$ and an amine in the process of this invention provides for periodic or continuous regeneration of the iron oxide bed and enhanced activity which in turn provides for effective removal of sulfur compounds from a gas stream.

Best Mode For Carrying Out The Invention

The following example is intended to illustrate and not to limit the scope of the present invention.

Analysis of the gas stream in the following example was conducted prior to and subsequent to treatment by the process of this invention. Gas samples were analyzed by a Barton Recording Sulfur Analyzer Model 286 by means of a slip stream. The Barton 286 Analyzer has a sensitivity of 0.02 ppm of $H_2S$ by volume, 0.02 ppm mercaptans by volume, 0.04 ppm organic sulfides by volume and 0.04 ppm sulfur dioxide with an accuracy of plus or minus 2%. Percent by volume reading were converted to percent by weight and recorded. (ppm equals parts per million.)

It should be noted that the following experiment was conducted on a commercial scale so as to illustrate the ability of the process of the present invention to fulfill a long-felt commercial need.

EXAMPLE 1

Addition of Concentrated Aqueous Ammonia Solution And $H_2O_2$ To A Ferric Oxide Bed The two treatment vessels used in this experiment were a 1.22 meter by 3.05 meter vertical cylindrical vessel with an approximate volume of 3.56 cubic meters. The treatment vessels were charged with 3.11 cubic meters of redwood chips coated with ferric oxide.

The redwood chips coated with ferric oxide were "IC" Shavings manufactured and sold by Connolly-GPM, Inc. of Chicago, Ill., which contains approximately 193.2 kilograms of $Fe_2O_3$ per cubic meter. A portion of the ferric oxide chips were added to each vessel. Water was added to give 5-10 percent by weight content and then the chips were compacted by tamping lightly. Then a layer of an alkaline material (specifically $Na_2CO_3$) was added. To one skilled in this art it would be evident that other material such as soda ash could be used. It has been found that addition of approximately one-half pound of soda ash per bushel of $Fe_2O_3$ provides the proper alkaline environment.

The process of chip addition, wetting with water, caustic addition and compaction, continued until the vessel was filled. In addition to the standard piping associated with iron sponge treaters were two smaller vessels used as holding tanks for the oxidant and amine. These two tanks were connected to the top of Number 1 treater by 21 feet of 0.25 inch stainless steel tubing connected to atomizing nozzles (internally placed in treater #1) through pressure tight connectors. The oxidant addition is accomplished by a system utilizing timers which permit precise amounts of oxidant to be introduced at specific times and in whatever sequence and quantity desired.

The gas subjected to treatment was taken from a wellhead which produces at approximately 1000 lbs. per square inch (6895 kPa) pressure. It contains an average of 200 ppm's sulfur compounds by weight. A typical wellhead sample relative to sulfur containing compounds was found to be:

since the iron sponge, in spite of $H_2O_2$ addition, would be unable to effect a sulfur reduction much below 35–40 ppm by weight.

Table II contains the pertinent data to the concurrent and simultaneous use of 16 N, $NH_4OH$ and 50 percent aqueous $H_2O_2$:

TABLE II

Addition of Concentrated Aqueous Ammonia Solution and $H_2O_2$ to Treater No. 1[1]

| Date | Time | Remarks | 16N Ammonium Hydroxide: Liters | 50% Hydrogen Peroxide: Liters | Sulfur Level: ppm by Wt | |
|---|---|---|---|---|---|---|
| | | | | | No 1 Treater Outlet | No 2 Treater Outlet |
| 11/15/81 | 1400 | Began pumping 50% $H_2O$ | | | 72 | 17 |
| | 1430 | Stopped pumping $H_2O_2$ - Began pumping 16N $NH_4OH$ | | 4.55 | 36 | 17 |
| | 1450 | | 2.75 | | 35 | |
| | 1510 | | 7.56 | | 35 | |
| | 1525 | Stopped pumping $NH_4OH$ - Began pumping $H_2O_2$ | 8.90 | | 36 | |
| | 1545 | | | | 18 | |
| | 1555 | Stopped pumping $H_2O_2$ - Began pumping $NH_4OH$ | | 4.12 | 15 | 10 |
| | 1610 | | 3.62 | | 24 | |
| | 1630 | | 8.45 | | 26 | |
| | 1635 | Stopped pumping $NH_4OH$ | 9.70 | | 26 | |
| | 1700 | Began pumping $H_2O_2$ | | | 34 | |
| | 1730 | Stopped pumping $H_2O_2$ | | 3.79 | 14 | |
| | 1740 | | | | 12 | 9 |
| 11/16/81 | 0730 | | | | 71 | 14 |
| | 1700 | | | | 76 | 15 |
| 11/17/81 | 0800 | Began pumping $H_2O_2$ | | | 76 | 17 |
| | 0835 | Stopped pumping $H_2O_2$ | | 3.79 | 37 | 16 |

[1]No. 1 Treater filled with spent iron-sponge and No. 2 Treater filled with partially-spent iron-sponge material.

TABLE I

| Wellhead Analysis of Natural Gas Sulfur Content | |
|---|---|
| S-Compound | ppm by wt. |
| $H_2S$ | 134.4 |
| $CH_3SH$ | 2.1 |
| $C_2H_5SH$ | 16.9 |
| $C_3H_7SH$ | 16.1 |
| $C_4H_9SH$ | 5.9 |
| Amyl Mercaptans | 1.7 |
| Sulfides | 12.9 |
| Others | 0.2 |
| Total | 190.2 |

Prior to treatment the gas was separated from any liquid or solid phase material.

The operating conditions are set out as follows:

| | |
|---|---|
| Gas Flow | 1400 mcf per day* |
| Vessel Pressure | Treater No. 1 - 215 psi (1482 kPa) |
| | Treater No. 2 - 208 psi (1434 kPa) |
| Treatment Temperature | 15°–19° C. |
| Concentration of $H_2O_2$ | 50% by weight |
| Concentration of $NH_3$ aqueous solution | 16 normal (hereinafter referred to as 16 N $NH_4OH$) |

*(mcf = thousand cubic feet)

The flow rate and pressure were established as set out above. The ability of the $Fe_2O_3$ bed to remove sulfur compounds was monitored for approximately 3 months. Initially the $Fe_2O_3$ bed was able to satisfactorily remove $H_2S$ and partially remove mercaptans, however, after 3 months appreciable amounts of mercaptans began to break through.

It was felt that testing the effect of ammonia in conjunction with an oxidant ($H_2O_2$) would be possible at the time the Number 1 treater was nearly exhausted. Testing at this time would allow for detection of substantial reduction in sulfur content of the exiting gas With reference to Table II it is demonstrated that at 1430 hours (after pumping $H_2O_2$ for 30 minutes) that the sulfur level in the Number 1 treater effluent was only reduced from 72 ppm to 36 ppm.

Immediate addition of 8.9 liters of 16 N ammonia (from 1430 to 1525 hours) had no further effect on the sulfur level. Thus, it would appear that addition of the amine alone, in the absence of the oxidant, did not provide the required removal ability. It must be remembered, however, ammonia will not decompose and will therefore slowly move through the bed (8 to 10 hours), primarily as aqueous ammonia hydroxide.

Evidence of a positive effect (i.e., an observable, appreciable reduction of gas sulfur level) is seen by following $NH_4OH$ addition with $H_2O_2$. This is evidenced by the data contained within Table II. At 1525 hours, $NH_4OH$ addition was stopped and $H_2O_2$ addition commenced. Within 20 minutes, the total sulfur level dropped from 36 ppm to 18 ppm in the Number 1 treater effluent. The cycle was repeated wherein pumping of $NH_4OH$ began at 1555 hours and stopped at 1635 hours. Then $H_2O_2$ introduction was started at 1700 hours and continued until 1730 hours. During this later time the sulfur level went from 34 ppm to 12 ppm.

The observe results, indeed, demonstrate that ammonia (or amines) when used in conjunction with an oxidant, (i.e., hydrogen peroxide or oxygen), used either consecutively or simultaneously, will result in a faster and more complete removal of sulfur-containing compounds from natural gas. It appears as if the unobvious and novel combination of an oxidant with an amine in a metal oxide treatment system evidences a synergistic effect. By synergistic effect is meant that the combination of the amine and oxidant will provide more effective removal of sulfur compounds from a gas stream than use of the amine or oxidant alone in an iron oxide treatment system. It is this discovery of a synergistic effect that forms at least a portion of the present invention.

Further, the data indicates that the process of the present invention has the advantage of more effective sulfur removal, which also requires less oxidant and in turn would then allow for the use of smaller treatment vessels. Thus, the process of the present invention provides for the extended life of the metal oxide bed which in turn substantially reduces the cost of such treatment systems.

The data presented clearly indicates that the process of the present invention is superior to that presently used and provides an unexpected result.

The data also indicates that the combination of an amine and an oxidant in a metal oxide treatment bed evidences synergism. By synergism is meant that the combined effect of using the amine and the oxidant together is greater than the sum of the effect of using the oxidant alone or the amine alone. It is this synergistic effect that provides the present invention with the ability to economically and effectively remove sulfur compounds from a gas stream.

This commercial-scale application of the present invention amply demonstrates the nonobvious advantages that can be obtained through the use of the process of this invention over the prior art.

The data just provided illustrates the use of the present invention in a two-stage treatment process. The process of the present invention is also adaptable to single or multi-stage treatment processes wherein the process described in this invention may precede or be subsequent to another treatment process. Also, two or more iron sponge beds may be used in series with peroxide and an amine addition.

It would be evident to those skilled in the art that the concentration of the $H_2O_2$ and the amine will depend upon the amount of, and sulfur level of the incoming gas and the restriction requirements on the sulfur content of the effluent.

Industrial Applicability

The process of this invention employs the use of an oxidant and an amine in conjunction with an oxide bed and as such has numerous industrial applications.

An effective and economical means of removing sulfur compounds, specifically $H_2S$, sulfides and disulfides, and mercaptans from a gas stream has long been needed. Through the use of this invention, sulfur compounds can be removed from a gas stream both economically and efficiently. For example, effluent from coke ovens, sewage plants, paper mills and in particular, sour natural gas streams can benefit from the process of the present invention. Conversely, this invention can be used to remove sulfur compounds from gas streams entering vessels, buildings, and etc.

While certain representative embodiments and details have been shown for the purpose of illustrating the invention, it will be apparent to those skilled in this art that various changes and modifications may be made therein without departing from the scope of the invention

We claim:

1. A process for removing hydrogen sulfide, sulfides and mercaptans from a gas stream which comprises the steps in combination of:
   (a) contacting the gas stream with an oxide of a metal selected from the group consisting of iron, chromium, cobalt, lead, manganese, molybdenum, nickel, copper, vanadium, zinc, tungsten, and antimony;
   (b) introducing ammonia onto the metal oxide; and
   (c) subsequently or concurrently introducing hydrogen peroxide onto the metal oxide while continuing to contact the gas stream with the metal oxide.

2. A process according to claim 1 wherein the treated gas stream is a natural gas stream.

3. A process according to claim 1 wherein the treated gas stream is subsequently treated until a desired level of $H_2S$ mercaptans and sulfides is obtained.

4. A process according to claim 1 wherein the oxidizing agent is aqueous hydrogen peroxide at a concentration of at least 25 percent by weight.

5. A process for removing hydrogen sulfide, sulfides and mercaptans from a gas stream which comprises the steps in combination of:
   (a) contacting the gas stream with a metal oxide in an alkaline environment, wherein the metal is selected from the group consisting of iron, cobalt, nickel and copper;
   (b) introducing ammonia continuously or intermittently in anhydrous form or aqueous solutions thereof onto the metal oxide; and
   (c) subsequently or concurrently introducing an oxidizing agent, continuously or intermittently, selected from the group consisting of oxygen, hydrogen peroxide, air, tertiary dibutyl peroxide, t-butyl hydroperoxide, cumene hydroperoxide and dicumyl peroxide, on the metal oxide while continuing to contact the gas stream with said metal oxide.

6. A process according to claim 5 wherein the alkaline environment is attained by the addition of a compound selected from the group consisting of NaOH, KOH and $Na_2CO_3$, to the metal oxide.

7. A process according to claim 5 wherein the metal oxide is iron oxide, the oxidizing agent is aqueous $H_2O_2$ at a concentration of at least 5 percent by weight and the ammonia is a saturated aqueous solution.

8. A process for removing sulfur compounds selected from $H_2S$, sulfides and mercaptans, from a gas stream wherein said gas stream is contacted with at least one metal oxide in an alkaline environment, the improvement comprising the introduction of hydrogen peroxide and ammonia on the metal oxide while continuing to contact the gas stream with said metal oxide.

9. A process according to claim 8 wherein the alkaline environment is attained by the addition of a compound selected from the group consisting of NaOH, KOH and $Na_2CO_3$, to the metal oxide.

10. A process for removing hydrogen sulfide, sulfides and mercaptans from gas streams which comprises the steps in combination of:
    (a) contacting the gas stream with an oxide of a metal selected from the group consisting of iron, chromium, cobalt, lead, manganese, molybdenum, nickel, copper, vanadium, zinc, tungsten and antimony;
    (b) introducing an amine, continuously or intermittently, of the structural formula:

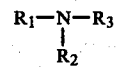

wherein $R_1$, $R_2$, and $R_3$ are selected from the group consisting of hydrogen, alkyls of 1 to 8 carbon atoms and alkanols of 1 to 8 carbon atoms with the proviso that $R_1$, $R_2$ and $R_3$ cannot all by hydrogen; in anhydrous form, aqueous solutions or water/alcohol solutions thereof, onto the metal oxide; and (c) subsequently or concurrently introducing an oxidizing agent, continuously or intermittently, selected from the group consisting of oxygen, hydrogen peroxide, air, tertiary dibutyl peroxide, t-butyl hydroperoxide, cumene hydroperoxide and dicumyl peroxide, on the metal oxide while continuing to contact the gas stream with said metal oxide.

11. A process according to claim 10 wherein the amine is introduced as a water/alcohol solution thereof, the alcohol is selected from the group consisting of methanol, ethanol, propanol and butanol.

* * * * *

UNITED STATES PATENT AND TRADEMARK OFFICE
CERTIFICATE OF CORRECTION

PATENT NO. : 4,435,371
DATED : Mar. 6, 1984
INVENTOR(S) : Kenneth J. Frech, James J. Tazuma It is certified that error appears in the above-identified patent and that said Letters Patent is hereby corrected as shown below:

Column 5, lines 6 through 11, delete the following:
"Of the metal oxides that are more useful in the process of the present invention are oxides of iron, cobalt and copper. Expecially preferred and useful in the process of the present invention is iron oxide ($Fe_2O_3$)."

and substitute therefor:

--Representative of the oxides that can be used in the process of the present invention are oxides of metals such as iron, chromium, cobalt, lead, manganese, molybdenum, nickel, copper, vanadium, zinc, tungsten and antimony. Of the metal oxides that are more useful in the process of the present invention are oxides of iron, cobalt and copper. Especially preferred and useful in the process of the present invention is iron oxide ($Fe_2O_3$).--

Column 8, line 5, delete "suynertistic" and substitute therefor --synergistic--.

Signed and Sealed this

Thirtieth Day of October 1984

[SEAL]

Attest:

GERALD J. MOSSINGHOFF

*Attesting Officer*   *Commissioner of Patents and Trademarks*